United States Patent [19]

Prewett et al.

[11] Patent Number: 5,314,476

[45] Date of Patent: May 24, 1994

[54] DEMINERALIZED BONE PARTICLES AND FLOWABLE OSTEOGENIC COMPOSITION CONTAINING SAME

[75] Inventors: Annamarie B. Prewett, Little Silver, N.J.; Roger C. Stikeleather, Doylestown, Pa.

[73] Assignee: Osteotech, Inc., Shrewsbury, N.J.

[21] Appl. No.: 119,882

[22] Filed: Sep. 10, 1993

Related U.S. Application Data

[63] Continuation of Ser. No. 830,934, Feb. 4, 1992, abandoned.

[51] Int. Cl.⁵ .......................... A61F 2/28; A61F 2/44; A61F 2/02; A61F 13/00
[52] U.S. Cl. ........................ 623/16; 623/11; 623/18; 424/422; 424/423
[58] Field of Search ............... 623/11, 16, 18; 606/77, 606/151; 424/422, 423, 424

[56] References Cited

U.S. PATENT DOCUMENTS

| | | | |
|---|---|---|---|
| 4,472,840 | 9/1984 | Jefferies | 623/16 |
| 4,932,973 | 6/1990 | Gendler | 623/16 |
| 5,053,049 | 10/1991 | Campbell | 623/16 |
| 5,073,373 | 12/1991 | O'Leary et al. | 424/422 |

OTHER PUBLICATIONS

Glowacki et al. "Application of the Biological Principle of Induced Osteogenisis for Craniofacial Defects", *The Lancet*, pp. 959-962, May 2, 1981.

Covey et al., "Clinical Induction of Bone Repair With Demineralized Bone Matrix or a Bone Morphogenetic Protein", *Orthopaedic Review*, vol. XVIII, No. 8, pp. 857-863 (Aug., 1989).

Habal et al., "Autologous Corticocancellous Bone Paste for Long Bone Discontinuity Defects: An Experimental Approach", *Annals of Plastic Surgery*, vol. 15, No. 2, pp. 138-142 (Aug., 1985).

*Primary Examiner*—David Isabella
*Assistant Examiner*—Dinh X. Nguyen
*Attorney, Agent, or Firm*—Dilworth & Barrese

[57] ABSTRACT

Demineralized bone particles having a median length to median thickness ratio of at least about 10:1 are incorporated in an osteogenic composition useful for repairing bone defects.

20 Claims, No Drawings

DEMINERALIZED BONE PARTICLES AND FLOWABLE OSTEOGENIC COMPOSITION CONTAINING SAME

This is a continuation of copending application Ser. No. 07/830,934 filed on Feb. 4, 1992, now abandoned.

BACKGROUND OF THE INVENTION

This invention relates to demineralized bone and to an osteogenic composition incorporating demineralized bone. More particularly, the invention relates to demineralized bone particles having a relatively high median length to median thickness ratio, e.g., as in the case of filaments and thin sheets, and to a flowable osteogenic composition containing such particles within a biocompatible fluid carrier.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *OrthoRaedic Review*, Vol. XVII, No. 8, pp. 857–863 (August, 1989). According to Habal et al., "Autologous Corticocancellous Bone Paste for Long Bone Discontinuity Defects: An Experimental Approach", *Annals of Plastic Surgery*, Vol. 15, No. 2, pp. 138–142 (August 1985), autogenous bone which has been granulated into a pastelike material and combined with autogenous blood has been used in the repair of long bone defects in dogs.

While it is known that bone particles possessing relatively high median length to median thickness ratios, e.g., filaments and thin sheets, can be obtained by milling bone, such particles are not known to have been subjected to demineralization, a process which results in the nearly complete removal of the inorganic components of the bone, largely hydroxy apatite, which gives bone its characteristic rigidity and structural properties.

U.S. Pat. No. 5,073,373 discloses a deformable, shape-sustaining osteogenic composition, suitable as a filler for osseous defects, in which particles of demineralized bone are uniformly distributed within a carrier which is a liquid polyhydroxy compound such as glycerol. The vast majority of the demineralized bone particles possess random, irregular geometries with an average median length to median thickness ratio of from about 1:1 to about 3:1.

SUMMARY OF THE INVENTION

It is an object of the invention to provide demineralized bone particles of relatively high median length to median thickness ratio and a flowable osteogenic composition containing the particles.

It is another object of the invention to provide a flowable osteogenic composition of putty-like consistency comprising demineralized osteogenic particles of relatively high median length to median thickness ratio and a biocompatible fluid carrier for the particles with or without such optional ingredients as thixotropic agents, therapeutic agents, and the like.

It is yet another object of the invention to provide a process for producing demineralized bone particles employing a delamination technique.

In keeping with these and related objects of the invention, there is provided a quantity of demineralized bone particles of which at least about 60 weight percent is made up of demineralized bone particles having a median length to median thickness ratio of at least about 10:1.

When a quantity of the foregoing bone particles is combined with an appropriate amount of a suitable biocompatible fluid carrier, e.g., a polyhydroxy compound such as glycerol, the resulting osteogenic composition assumes a flowable state. Compared with the osteogenic composition of aforementioned U.S. Pat. No. 5,073,373 which utilizes demineralized bone particles of relatively low median length to median thickness ratio, the osteogenic composition herein tends to more readily retain its shape due, it would appear, to the tendency of the bone particles to become entangled with each other. The ability of the osteogenic composition to maintain its cohesiveness and to resist erosion subsequent to being applied to an osseus defect site is highly advantageous since it provides optimum utilization of the available bone particles.

Application of the foregoing osteogenic composition to the site of a bone defect, e.g., one resulting from injury, infection, malignancy or developmental malformation, leads to rapid new bone ingrowth by one or more mechanisms such as osteogenesis, osteoconduction and/or osteoinduction. The osteogenic composition can be prepared when and as needed by mixing the demineralized bone particles with the fluid carrier or the composition can be prepared well in advance of its use and stored in the sterile condition until needed.

The expression "median length to median thickness ratio" as applied to the demineralized bone particles of this invention shall be understood to refer to the ratio of the longest median dimension of a bone particle (its median length) to its shortest median dimension (its median thickness).

The term "flowable" as applied to the osteogenic composition of this invention shall be understood to refer to the ability of the composition to flow either of its own accord or under the influence of some moderate amount of mechanical force, e.g., as exerted by the plunger element of a syringe. Thus, osteogenic compositions of paste-like or putty-like consistency as well as those of liquid or runny consistency are properly referred to as "flowable" within the context of the present invention.

The term "fluid" as applied to the biocompatible carrier component of the osteogenic composition shall be understood to refer to those materials that are liquid at ambient temperature or are plastically deformable by hand at ambient temperature.

DESCRIPTION OF THE PREFERRED EMBODIMENTS

Bone particles whose median length to median thickness ratio is at least about 10:1 can be readily obtained by any one of several methods, e.g., shaving the surface of an entire bone or relatively large section of bone. Employing a shaving technique, particles ranging in median length from about 2 mm up to about 400 mm or more (as in the case of the long bones) and in median thickness from about 0.05 mm to about 2 mm can be obtained. Another procedure for obtaining the bone particles herein, particularly useful for pieces of bone of up to about 100 mm in length, is the Cortical Bone Shredding Mill available from Os Processing Inc., 3303 Carnegie Avenue, Cleveland, Ohio 44115.

Depending on the procedure employed for producing the bone particles, one can obtain a mass of bone particles containing at least about 60 weight percent, preferably at least 70 weight percent and most preferably at least about 80 weight percent of bone particles possessing a median length of from about 2 mm to about 400 mm or more and preferably from about 10 mm to about 100 mm, a median thickness of from about 0.05 mm to about 2 mm and preferably from about 0.08 mm to about 1.5 mm, and a median length to median thickness ratio of at least 10:1 up to about 500:1 or more and preferably from about 50:1 to about 100:1. if desired, the mass of bone particles can be graded into different sizes and/or reduce or eliminate any less desirable size(s) of particles which may be present. In overall appearancer the bone particles can be described as filaments, threads, narrow strips, or thin sheets. Often, where thin sheets are produced, their edges tend to curl up toward each other. The bone particles can be obtained from cortical, cancellous and/or corticocancellous bone which may be of autogenous, allogeneic and/or xenogeneic origin. Porcine bone is a particularly advantageous type of xenogeneic bone tissue which can be used as a source for the demineralized bone particles of this invention.

Following shaving, milling or other technique whereby they are obtained, the bone particles are subjected to demineralization in order to reduce their inorganic content to a very low level, e.g., to not more than about 1% by weight of residual calcium and preferably to not more than about 0.5% ppm by weight residual calcium. Demineralization of the bone particles ordinarily results in their contraction to some extent.

Demineralization of the bone particles can be conducted in accordance with known and conventional procedures. In a preferred demineralization procedure, the bone particles are subjected to a defatting/disinfecting step which is followed by an acid demineralization step. A preferred defatting/ disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Following defatting, the bone is immersed in acid over time to effect its demineralization. Acids which can be employed in this step include inorganic acids such as hydrochloric acid and organic acids such as peracetic acid. After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Further in accordance with invention, the demineralized bone particles can be used immediately for preparation of osteogenic composition or they can be stored under aseptic conditions, advantageously in a lyophilized state, prior to such preparation.

Another process for obtaining the bone particles of this invention employs a fluid particulation technique. In accordance with this process, the bone selected as the source of the particles is first demineralized, advantageously by the preferred demineralization procedure described above, and thereafter lyophilized in accordance with procedures and conditions which are well known in the art, e.g., a shelf temperature of from −20° C. to about −35° C., a vacuum of from about 150–100 mTorr and a time period of from abut 4 to about 48 hours depending on the mass of particles being processed. The demineralized, lyophilized bone particles are then immersed in a fluid, e.g., water, aqueous solution of propylene glycol or other osmotic swelling agent such as pH 2 buffer or lyotropic swelling agent, and the entire mass slowly stirred for one or more hours or until a significant quantity of particles possessing the required relative dimensions is obtained. Unlike a milling operation which produces bone particles from the bone source by a shearing action, the foregoing fluid particulation process appears to produce the demineralized bone particles of this invention by a delamination action. Following removal of the fluid used in the process, e.g., by filtration, the bone particles are dried and then utilized in the preparation of osteogenic composition or stored in the sterile condition as in the case of bone particles obtained by the milling technique.

To prepare an osteogenic composition utilizing the demineralized bone particles of this invention, a quantity of the particles are combined with an amount of biocompatible fluid carrier which will provide a flowable mass. In a preferred embodiment of the osteogenic composition, the carrier is a polyhydroxy compound or derivative thereof which, if necessary or desirable, can be dissolved or diluted with an appropriate solvent to provide a readily deformable mass with some ability to retain its shape over the relatively short term, e.g., for 10 minutes to several hours or even days. Thus, the polyhydroxy compound or polyhydroxy derivative can be a liquid in the pure or highly concentrated state at ambient temperature, e.g., 15°–50° C., or it can be a solid or semi-solid at this temperature in which case it becomes necessary to dissolve the material in a solvent such as water, physiological saline, ethanol, glycerol, glucose, propylene glycol, polyethylene glycol of from 200–1000 molecular weight, polyvinyl alcohol, etc. Of course, the carrier can be made up of one or more liquid polyhydroxy compounds or derivatives in solution with one or more solid polyhydroxy compounds or derivatives.

Useful polyhydroxy compounds possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include ethylene glycol, diethylene glycol, triethylene glycol, 1,2-propanediol, glycerol, trimethylolethane, trimethylolpropane, erythritol, pentaerythritol, polyalkylene glycols such as the polyethylene glycols, xylitol, sorbitol, mannitol, dulcitol, arabinose, xylose, ribose, adonitol, arabitol, rhamnose, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

Derivatives of the foregoing polyhydroxy compounds, in particular, ester derivatives thereof, are also useful. For example, liquid and solid monoesters and diesters of glycerol can be used to good effect, the solid esters being dissolved up to the limit of their solubilities in a suitable vehicle, e.g., propylene glycol, glycerol, polyethylene glycol of 200–1000 molecular weight, etc. Liquid glycerol esters include monacetin and diacetin and solid glycerol esters include such fatty acid monoesters of glycerol as glycerol monolaurate, glyceryl monopalmitate, glyceryl monostearate, etc. An especially preferred carrier herein comprises glyceryl monolaurate dissolved in glycerol or a 4:1 to 1:4 weight mixture of glycerol and propylene glycol.

Of the foregoing polyhydroxy compounds, glycerol and its liquid monoesters and diesters, e.g., monacetin and diacetin, fructose, glucose and sucrose, and mixtures thereof are preferred. Where the polyhydroxy compound is a solid, e.g., sucrose, a solvent such as water, glycerol, polyethylene glycol of from 200–1000 average molecular weight, or mixture thereof is used to provide a flowable solution or paste of the compound.

Where, in a particular osteogenic composition, the bone particles exhibit a tendency to quickly or prematurely separate from the carrier component or to otherwise settle out from the composition such that application of a fairly homogeneous composition is rendered difficult or inconvenient, it can be advantageous to include within the composition a substance whose thixotropic characteristics prevent or reduce this tendency. Thus, e.g., where the carrier component is glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, etc., can be combined with the carrier in an amount sufficient to significantly improve the suspension-keeping characteristics of the composition.

If desired, the demineralized bone particles of this invention can be modified in one or more ways, e.g., their protein content can be augmented or modified as described in U.S. Pat. Nos. 4,743,259 and 4,902,296. Any of a variety of medically and/or surgically useful substances can be incorporated in, or associated with, the demineralized bone particles either before, during or after preparation of the osteogenic composition. Thus, e.g., one or more of such substances can be introduced into the demineralized bone particles, e.g., by soaking or immersing the bone particles in a solution or dispersion of the desired substance(s), by adding the substance(s) to the carrier component of the osteogenic filler composition or by adding the substance(s) directly to the filler composition.

Medically/surgically useful substances which can be readily combined with the demineralized bone particles and/or osteogenic composition of this invention include, e.g., demineralized bone powder as described in aforementioned U.S. Pat. No. 5,073,373, collagen, insoluble collagen derivatives, hydroxy apatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

As previously indicated, the osteogenic composition of this invention can be freshly prepared just by mixing desired quantities of the demineralized bone particles, fluid carrier and optional component(s), if any, in any suitable sequence of separate mixing operations or all at once. Thus, the demineralized bone particles can be mixed with the optional ingredient(s) and thereafter combined with the carrier component, the demineralized bone particles can be mixed with the carrier followed by addition of the optional ingredient(s) or the optional ingredients can be added to the carrier followed by addition of the demineralized bone particles. Variations of these and other sequences of mixing are, of course, possible.

The amount of demineralized bone particles which can be incorporated into the osteogenic composition can vary widely with amounts of from about 5 to about 90 weight percent, and preferably from about 20 to about 80 weight percent, being entirely suitable in most cases, the balance of the composition being made up of carrier and optional ingredient(s), if any. To facilitate on-site preparation of the composition herein, the demineralized bone particles, preferably in lyophilized form, and fluid carrier (the latter containing one or more optional ingredients such as those identified above) can be stored in separate packages or containers under sterile conditions and brought together in intimate admixture at the moment of use for immediate application to an osseous defect site employing any suitable means such as a spatula, syringe, etc. Alternatively, the osteogenic composition can be prepared well in advance and stored under sterile conditions until required for use.

The osteogenic composition can be utilized for a variety of orthopaedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacements, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc.

The following examples are illustrative of the preparation of the demineralized, osteogenic bone particles of this invention and the preparation of an osteogenic composition containing the particles.

EXAMPLE 1

A section of allogenic cortical bone approximately 9 cm long and 10–30 mm wide is placed in the hopper of a Cortical Bone Shredding Mill of Os Processing, Inc., 3303 Carnegie Avenue, Cleveland, Ohio 44115 equipped with a 20-flute rotary cutter. The mill was operated at a speed of about 120 rpm until approximately 100 to 1000 g of mass of bone particles of which at least 80 weight percent is made up of particles having a median length of about 10 mm and a median thickness of about 0.5 mm is obtained. The bone particles are then placed in a reactor. A 70 weight percent ethanol solution at a rate of 30 milliliters per gram of bone particles is introduced into the reactor followed by agitation for 1 hour (Bolander et al., *Journal of Bone and Joint Surgery*, Vol. 68-A, No. 8 (October 1986)) to effect defatting and disinfecting of the bone particles. Following drainage of the ethanol, a 0.6N solution of HCl at 50 ml per gram of bone is introduced into the reactor (Bolander et al., .), the reaction proceeding for 3 hours (Glowackie, *AATB Workshop*, 11th Annual meeting (1987)). Following drainage of the HCl, the bone particles are covered and rinsed three times with water for injection (WFI) with the WFI being replaced at 5 minute intervals. Following drainage of the WFI, the bone particles are completely covered with 0.1M sodium phosphate, a procedure which is repeated until the pH of the solution falls between 6.8 and 7.4. The rinsing procedure with WFI is repeated to provide demineralized, flexible elongate osteogenic bone particles containing not more than about 0.5 weight percent residual calcium.

EXAMPLE 2

The demineralized osteogenic bone particles from Example 1 (100 g) and injectable grade glycerol as the carrier (570 g) are thoroughly mixed to provide an osteogenic composition of putty-like consistency. The composition is readily applied to an osseous defect site, e.g., employing a syringe, spatula or other suitable device.

The ability of the foregoing osteogenic composition to maintain cohesion in an aqueous envirorment is compared with that of a like quantity of osteogenic composition prepared in accordance with U.S. Pat. No. 5,073,373. The latter composition contains a quantity of demineralized bone powder (100 g) of which at least 80 weight percent is made up of particles having a length to thickness ratio of from about 1:1 to about 3:1, and glycerol as the carrier (570 g). Employing a dropper, a few water droplets are allowed to fall from a height of just a few centimeters upon a quantity of each osteogenic composition. As the water droplets contact the osteogenic composition prepared with the bone powder, numerous individual particles of demineralized bone will be seen entering the water phase. However, in the case of the osteogenic composition of this invention, far fewer demineralized bone particles will enter the water phase. After 15 minutes from the initial contact of each osteogenic composition with the water droplets, the osteogenic composition herein will have maintained a far higher level of cohesiveness than the osteogenic composition prepared with the demineralized bone powder.

What is claimed is:

1. A flowable osteogenic composition comprising a quantity of entangled demineralized bone particles of which at least about 60 weight percent of said particles is made up of demineralized bone particles substantially in the shape of threads or filaments having a median length to median thickness ratio of at least about 10:1 and up to about 500:1, a median length of from about 2 mm to about 400 mm and a median thickness of from about 0.05 mm to about 2 mm and a sufficient amount of biocompatible fluid carrier to provide a flowable mass, whereby said osteogenic composition maintains its cohesiveness and resists erosion subsequent to being applied to an osseus defect site.

2. The osteogenic composition of claim 1 of which at least about 60 weight percent of said particles is made up of demineralized bone particles possessing a median length of from about 10 mm to about 100 mm, a median thickness of from about 0.08 mm to about 1.5 mm and a median length to median thickness ratio of from about 50:1 to about 100:1.

3. The osteogenic composition of claim 1 in which the demineralized bone particles are obtained from cortical autogenic, cortical allogeneic, cortical xenogeneic, cancellous autogenic, cancellous allogeneic, cancellous xenogeneic, corticocancellous autogenic, corticocancellous allogeneic or corticocancellous xenogeneic bone.

4. The osteogenic composition of claim 1 in which the demineralized bone particles are obtained from porcine bone.

5. The osteogenic composition of claim 1 containing from about 5 to about 90 weight percent demineralized bone particles and from about 10 to about 95 weight percent carrier.

6. The osteogenic composition of claim 1 containing from about 20 to about 80 weight percent demineralized bone particles and from about 20 to about 80 weight percent carrier.

7. The osteogenic composition of claim 1 wherein the carrier is a member of the group consisting of liquid polyhydroxy compound, liquid polyhydroxy compound derivative, liquid solution of solid polyhydroxy compound, liquid solution of solid polyhydroxy compound derivative and mixtures thereof.

8. The osteogenic composition of claim 7 wherein the carrier is selected from the group consisting of glycerol glycerol monoester and glycerol diester.

9. The osteogenic composition of claim 7 wherein the carrier is selected from the group consisting of monosaccharide, monosaccharide derivative, disaccharide, disaccharide derivative, oligosaccharide, oligosaccharide derivative and mixtures thereof.

10. The osteogenic composition of claim 7 wherein the carrier is selected from the group consisting of fructose, glucose and mixtures thereof.

11. The osteogenic composition of claim 7 wherein the carrier is a liquid solution of sucrose.

12. The osteogenic composition of claim 7 wherein the carrier is an aqueous solution of sucrose.

13. The osteogenic composition of claim 7 wherein the carrier is a liquid solution of a fatty acid monoester of glycerol.

14. The osteogenic composition of claim 7 wherein the carrier is a fatty acid monoester dissolved in a solvent which is selected from at least one of a different liquid polyhydroxy compound and derivative of said different liquid polyhydroxy compound.

15. The osteogenic composition of claim 7 wherein the carrier is a fatty acid monoester dissolved in a solvent selected from the group consisting of propylene glycol, glycerol, monoacetin, diacetin, liquid polyethylene glycol and mixtures thereof.

16. The osteogenic composition of claim 7 wherein the carrier is glycerol monolaurate dissolved in a solvent.

17. The osteogenic composition of claim 7 wherein the carrier is glycerol monolaurate dissolved in a solvent which is a different liquid polyhydroxy compound and/or derivative thereof.

18. The osteogenic composition of claim 7 wherein the carrier is glycerol monolaurate dissolved in a solvent selected from the group consisting of propylene glycol, glycerol, monoacetin, diacetin, liquid polyethylene glycol and mixtures thereof.

19. The osteogenic composition of claim 1 containing at least one additional ingredient selected from the group consisting of antiviral agent, antimicrobial agent, antibiotic agent, amino acid, peptide, vitamin, inorganic element, protein synthesis co-factor, hormone, endocrine tissue, synthesizer, enzyme, polymer-cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxy apatite and penetration enhancer.

20. The osteogenic composition of claim 1 wherein the entangled particles are thoroughly mixed in the carrier.

* * * * *